United States Patent [19]
Baro et al.

[11] 4,399,809
[45] Aug. 23, 1983

[54] ARTIFICIAL SPHINCTER FOR USE AT STOMA, OR FOR THE LIKE PURPOSES

[76] Inventors: Juan V. Baro, Mtrio de Urdax No. 15, Atico, Pamplona; Hector O. Hurtado, Paseo Sarasate No. 7, Secto Izqda, Pamplona, both of Spain

[21] Appl. No.: 200,479

[22] Filed: Oct. 24, 1980

[30] Foreign Application Priority Data

| Oct. 30, 1979 [ES] | Spain | 485537 |
| May 20, 1980 [ES] | Spain | 491637 |
| May 20, 1980 [ES] | Spain | 491638 |

[51] Int. Cl.³ ............................................... A61F 1/00
[52] U.S. Cl. .................................. 128/1 R; 128/327; 128/346; 128/DIG. 25; 3/1
[58] Field of Search .............. 128/DIG. 25, 1 R, 1 D, 128/344, 346, 325, 686, 283, 327; 3/1

[56] References Cited

U.S. PATENT DOCUMENTS

| 3,049,125 | 8/1962 | Kriwkowitsch | 128/344 X |
| 4,141,364 | 2/1979 | Schultze | 128/344 X |
| 4,183,102 | 1/1980 | Guiset | 128/344 X |

FOREIGN PATENT DOCUMENTS 2343183  5/1974  Fed. Rep. of Germany ...... 128/686

OTHER PUBLICATIONS

Timm et al., "Intermittent Occlusion System," IEEE Transactions on Bio-Medical Engineering, (Oct. 1970), p. 352.

*Primary Examiner*—Michael H. Thaler
*Attorney, Agent, or Firm*—Ostrolenk, Faber, Gerb & Soffen

[57] ABSTRACT

The invention concerns an artificial sphincter comprised of a strip to be wrapped around the intestine, conduit, tube of the wearer's body, or the like. The strip carries either a single inflatable chamber that extends along its length, or parallel longitudinally extending chambers, or rows of separate chambers, wherein the chambers in adjacent rows are staggered longitudinally along the strip. Passages communicate among the chambers to maintain uniform pressure. A tube communicates into the chambers for selectively delivering fluid to inflate them or to permit them to be deflated. At least one wall of the chamber is flexible and elastic, and that wall faces in around the intestine, or the like, so that upon inflation of the chambers, the intestine, conduit, tube or the like is compressed and occluded. In a variant, the chambers are shaped to have a smaller cross-section toward one longitudinal edge of the strip and a larger cross-section toward the other longitudinal edge thereof.

11 Claims, 9 Drawing Figures

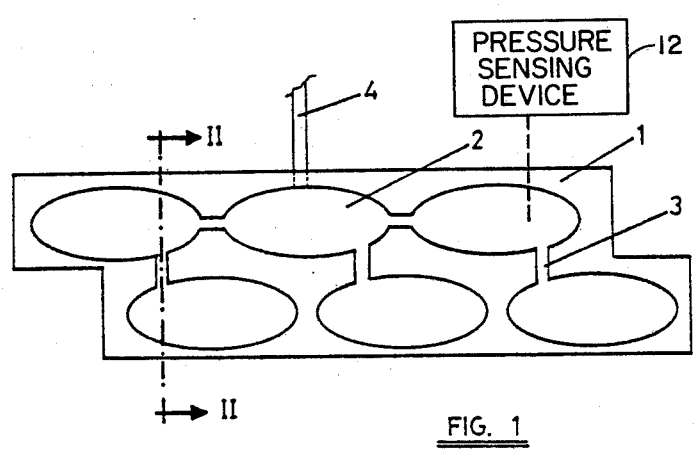
FIG. 1
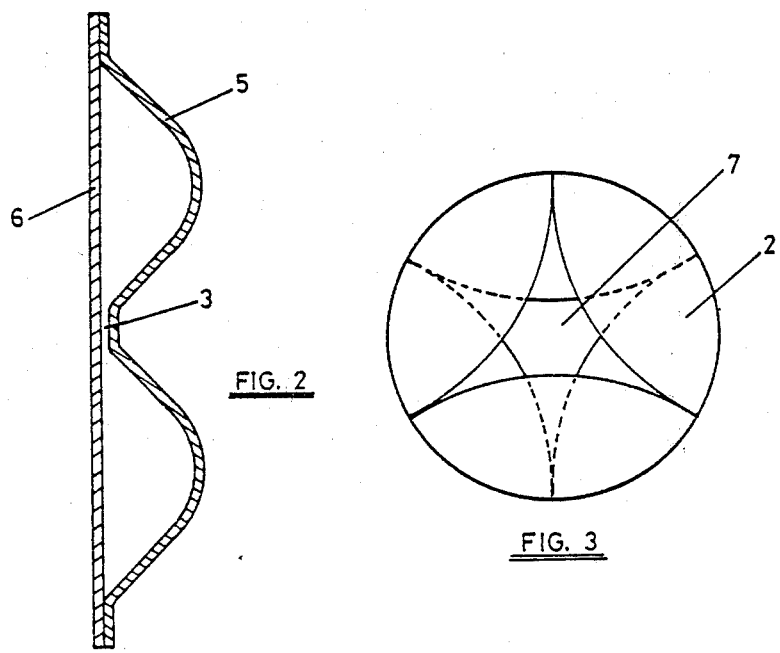
FIG. 2
FIG. 3

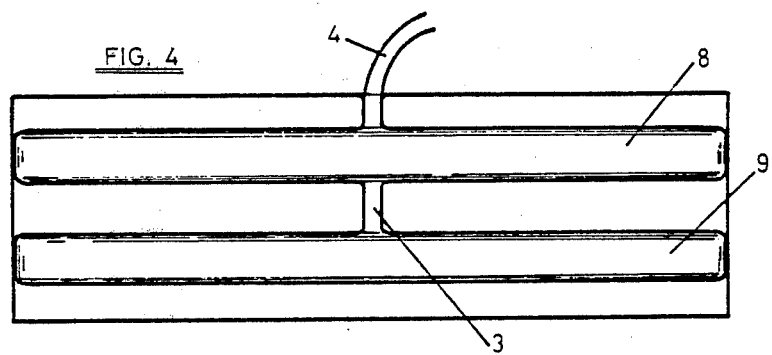
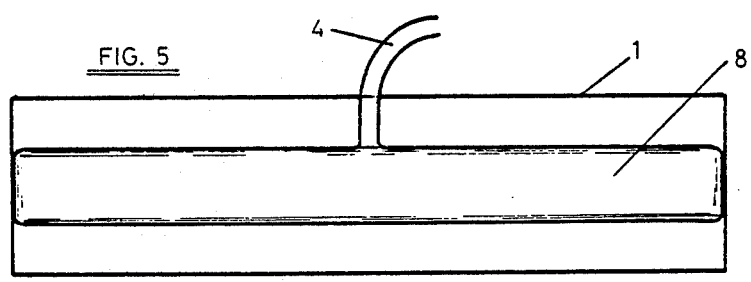
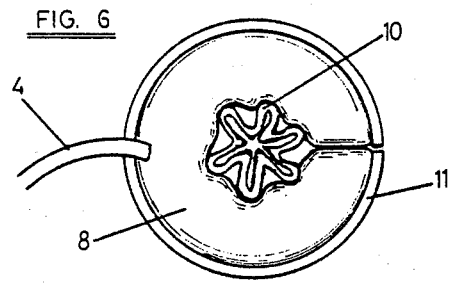

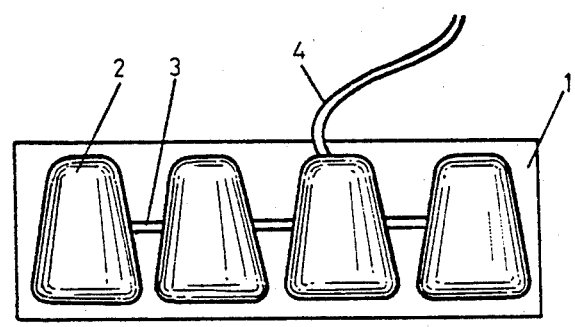
FIG. 7
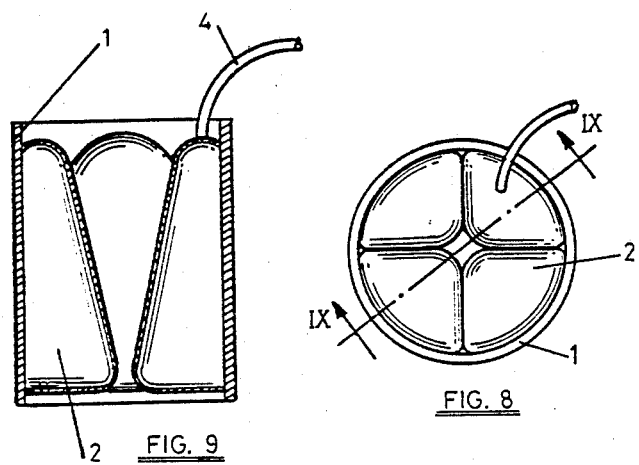
FIG. 8
FIG. 9

ARTIFICIAL SPHINCTER FOR USE AT STOMA, OR FOR THE LIKE PURPOSES

BACKGROUND OF THE INVENTION

The present invention relates to apparatus intended to ensure continence of stomas of the digestive system, both abdominal and perineal, and to prevent anal incontinence. The invention thus concerns an artificial sphincter for selectively compressing and occluding an opening at a stoma, or an opening in the intestine, or an opening in another tube section of the body.

To ensure continence of stomas in tubes or conduits of the digestive system, a stoma plug is now used, which may be an apparatus known by the trademark MACLET. An example of a plug of this type can be found in U.S. Pat. No. 3,952,726. This stoma plug is comprised of two parts, a magnetic ring that is placed around the intestine inside the wearer's body at the stoma and a magnetic plug that is inserted into the stoma and is held in place by the magnetic attraction of the ring. This apparatus has provided satisfactory results only in colostomies, but not in ileostomies. Furthermore, the apparatus cannot be applied to the perineal region.

SUMMARY OF THE INVENTION

The object of the present invention is to provide an apparatus which can be applied in stomas at any location in the body, and which can be used in any type of stoma and which can also be used to prevent anal incontinence. Furthermore, the apparatus may be more generally used any place along the intestine and even more generally in any conduit or tube of the body, principally in the digestive system.

The apparatus of the invention is characterized by comprising an artificial sphincter formed of a flexible band or strip, which has at least one longitudinally extending row, and more typically has at least two longitudinally rows, of inflatable chambers or bubbles defined on it, wherein the chambers in each row are preferably staggered with respect to the chambers in the adjacent rows. The chambers have and are defined by hermetically sealed walls, at least one of which is flexible and may be elastic as well. In addition, the chambers are interconnected for maintaining substantially uniform pressure among them. A conduit is connected between one of the chambers and a suction-impeller pump that is located subcutaneously in the wearer's body. The pump selectively introduces or extracts a fluid for inflating and emptying the separate chambers. When the chambers are filled, they are inflated to their maximum capacity. When the chambers are evacuated, they are deflated, and the two walls of each chamber almost lie against each other.

The strip or band of chambers is intended to be wrapped around the outside of the intestine near the stoma. Once the strip has been arranged in this manner, the plunger of a control valve is actuated, and the pump aspirates the content of the chambers, evacuating them, whereby the artificial sphincter is decompressed and the intestine is not compressed and occluded. On the other hand, when the pump pumps the fluid, the fluid is again forced into the chambers, and they are inflated to a predetermined pressure. This compresses and occludes or closes the encircled conduit or tube in the digestive system, e.g. the encircled intestine, thus avoiding the discharge of solid, liquid or gaseous contents.

The apparatus of the invention can be provided with an electronic sensing device for advising the wearer that the pressure within his digestive system tube i.e. his intestine, has reached a predetermined level, which make it advisable to decompress the artificial sphincter.

The artificial sphincter of the invention may be constructed in different forms and with different dimensions depending on the requirements and intended use. For example, the band or strip thereof may have a height, i.e. a width dimension, of 1 to 1½ cm, a longitudinal length which varies depending on the circumference of the ostomy of the patient, for instance between 6 and 12 cm, and a thickness of 2 mm. In one preferred embodiment, the strip comprises two rows of three chambers each, and the chambers of the neighboring rows are staggered with respect to each other, and are arranged close together. Each chamber has a height, i.e. a dimension along the width dimension of the strip, of 0.5 to 0.75 cm. The length of the chambers may vary between 2 and 4 cm.

The separate chambers communicate with each other. All of the chambers are charged and discharged through a tube which extends from one of the chambers, and this tube extends up to the pump chamber of the manually actuated suction-impeller pump.

Two walls of the band define each chamber. The walls are at opposite surfaces of the strip or band. The chamber wall which will be directed toward the tube of the wearer's body, e.g. the intestine, may have greater flexibility than the other outer wall of the chamber, so that upon inflation or deflation, each chamber experiences only expansion and protrusion of the inner wall. In addition to being flexible, the inner wall of the chamber may be elastic.

The artificial sphincter with its chambers, as well as the outlet tube for transferring fluid to and from the chambers preferably is formed of silicone or some other material of similar properties which is tolerated by the body.

On one of the sides of the artificial sphincter, there may be placed a plate of different material which permits better anchoring in the tissue and stimulates fibrosis, such as well known materials identified by the trademarks Teflon, Dacron, as well as other materials.

In a variant of the invention, the chambers of each row may be extended in the longitudinal direction so as to interconnect with each other, thereby actually defining a single hermetically sealed chamber in each row. Each such chamber is then of sufficient length to surround the conduit or tube of the body, i.e. the intestine.

In accordance with this variant, the artificial sphincter may be formed of a single longitudinally extending hermetically sealed chamber or else of two parallel, longitudinally extending and intercommunicating chambers. Furthermore, if desired the sphincter could comprise more than two parallel chambers.

In the case of both one or two parallel chambers, the chambers may have an open configuration. Then their closed ends are close together and even attached to each other when the chamber or chambers are wrapped around the intestine.

The chamber or chambers may alternatively be of continuous annular configuration.

In accordance with still another variant, a single row of chambers is provided. The chambers each have a vertical course and they are located near to each other. When the support band is closed around the intestine, and when these chambers are inflated, they contain the body conduit or tube, e.g. the intestine within them and close the passage through the conduit.

The chambers may also be of a cross-section which decreases from one end thereof to the opposite end, measured across the width dimension of the strip, with the cross-section of all of all of the chambers increasing in the same direction.

In order that the artificial sphincter of the invention may be more easily understood, a detailed description appears below with reference to the accompanying drawings, in which a few embodiments are shown, by way of illustration and not of limitation.

In the drawings, identical parts or parts of identical function have been designated by the same reference numbers.

BRIEF DESCRIPTION OF THE DRAWINGS

FIG. 1 is an elevational view of one embodiment of a band or strip which constitutes the artificial sphincter of the invention.

FIG. 2 is a cross-sectional view on a larger scale, along the line II—II of FIG. 1.

FIG. 3 is a plan view, on a larger scale, of the shaped artificial sphincter of FIG. 1, as it would appear when wrapped around an intestine.

FIGS. 4 and 5 are plan views of artificial sphincters in accordance with two variants of the invention.

FIG. 6 is a profile view of the artificial sphincter of either of FIGS. 4 or 5 mounted around an intestine, and with the chamber or chambers of the sphincter inflated.

FIG. 7 is a plan view in its extended position of another variant of artificial sphincter according to the invention.

FIG. 8 corresponds to a plan view of a sphincter, with the band or strip which serves as support for the chambers closed, and with the chambers inflated.

FIG. 9 is a cross-sectional view along the line IX—IX of FIG. 8.

DESCRIPTION OF THE PREFERRED EMBODIMENTS

The artificial sphincter of FIG. 1 is formed from a band or strip 1 of a suitable material, such as silicone, on which a number of shaped chambers or bubbles 2 with hermetically sealed walls are formed. The chambers communicate with each other through small passageways 3, so that the pressure which prevails in all of the chambers is approximately the same.

From one of the chambers 2, a conduit 4 extends to a manually operated suction-impeller pump (not shown), which may be of any known nature. The pump will operate in such a manner that when the valve is depressed, the fluid contained in the chambers 2 is aspirated, emptying them, whereby the two opposed walls on opposite surfaces of the strip 1, which walls define each of the chambers, come against each other. On the other hand, when the pump is actuated, the fluid is forced into the chambers 2, which will then be inflated.

As shown in FIG. 2, the chambers are all comprised of one component wall 5 of the strip 1, which wall has greater flexibility than the other component wall 6 of the strip 1. The wall 5 may furthermore be elastic in nature. The wall 5 of greater flexibility will be the wall which faces the intestine when the sphincter is wrapped around the intestine.

In FIG. 1, the strip 1 comprises two rows of chambers 2, which are aligned in each row. The chambers of one row are staggered with respect to the chambers of the other row. FIG. 2 shows the intercommunication passage 3 between two chambers, which is defined between the walls 5 and 6 that define all of the chambers.

The wall 6 may be covered on one of its faces by a material which facilitates its anchoring to the body tissue. This material may consist of a material known by the trademark Teflon or Dacron, etc.

The strip or band shaped sphincter of FIG. 1 is arranged in the manner shown in FIG. 3, being wound around the outside of the intestine near the stoma. The ends of the strip or band are connected to each other to form a closed encircling band. When the chambers 2 are inflated, this reduces the central space 7 occupied by the intestine to a minimum, and the intestine will be subjected to pressure, and will b compressed and occluded, preventing the discharge of solid, liquid and even gaseous elements past the inflated sphincter. When the pump is operated, the chambers 2 are deflated, and the pressure on the stoma is released permitting the discharge of the elements contained in the intestine.

As already indicated, there may be placed in the intestine near the stoma an electronic sensing device 12 which advises the wearer when a given pressure has been reached in the intestine at which decompression of the sphincter by operation of the pump is advisable.

Referring to FIG. 4, the plurality of chambers of each row shown in FIG. 1 are replaced by two hermetically sealed, longitudinally extending, continuous chambers 8 and 9. They are connected together by the passage 3. One of the chambers, in this case the chamber 8, has a conduit 4 for the introduction and removal of the fluid used to inflate and deflate the chambers.

In the embodiment of FIG. 5, there is only a single, hermetically sealed, continuous, longitudinally extending chamber 8 from which the inlet and outlet conduit 4 extends.

As can be seen from FIG. 6, the strip or band 1 with its chambers 8 and 9 is wrapped around the outside of the intestine 10. The transverse or longitudinal end edges of the strip 1 are connected together, or else the closed ends of the chamber or chambers are connected, in the event that there is no said strip.

Upon inflation of the chamber or chambers 8 and 9, the intestine 10 is compressed and occluded so as to prevent passage of material through it. On the other hand, upon deflation of the chamber or chambers 8 and 9, the intestine 10 can expand, permitting passage of material through it.

The chambers 8 and 9 may, as shown in FIGS. 4 and 5, have an open configuration or else have a continuous closed configuration, defining a ring which is wrapped around the intestine 10.

The wall of the chambers 8 and 9 which faces toward the intestine 10 may be flexible and elastic, while the strip is reinforced on the outside so that it cannot expand outward upon inflation of the chambers. The reinforcement may comprise, for instance, a semirigid ring 11. This ensures that upon inflation of the chambers 8 and 9, their expansion will take place in the radially inward direction so as to compress the intestine 10.

The ring 11 may be split in the event that the chambers 8 and 9 have the configuration shown in FIGS. 4 and 5, so as to permit mounting of the ring. If the chambers are continuous annular chambers, the ring 11 may be a closed ring.

As shown in FIGS. 7 through 9, the chambers 2 may each have a cross-section which increases towards one of the long side edges of the strip 1 so that when the chambers are inflated, the pressure which may prevail within the intestine presses with greater force against the upper part of the chambers 2 of smaller cross-section, while the lower part of the chambers 2 will compress the intestine with greater pressure, thus assuring closure of the passage through the intestine.

In a simpler configuration, the chambers 2 could be developed in the form of vertical cylindrical chambers, approximately tangent to the band or strip 1.

The present invention may be embodied in other specific forms without departing from the spirit or essential attributes thereof, and, accordingly, reference should be made to the appended claims, rather than to the foregoing specification, as indicating the scope of the invention.

What is claimed is:

1. An artificial sphincter for ensuring continence of stomas of the digestive system, for preventing anal incontinence, for occluding conduits and tubes in the digestive system of the body, and for like purposes, the artificial sphincter comprising:
   - a flexible band bendable into a cylindrical form adapted to encircle the intestine or other conduit or tube of the body, or the like, which is to be compressed and occluded;
   - inflatable chamber means defined in said band, said chamber means having a flexible wall and comprising a first plurality of chambers disposed in a first row and a second plurality of chambers disposed in a second row spaced apart from said first row along the axis of said chamber, the chambers of said first row being staggered with respect to said chambers of said second row, each said row extending the length of said band;
   - a conduit for transmitting fluid to said inflatable chamber means for selectively inflating and deflating said chamber means; and
   - passages connecting said chambers for establishing uniform pressure among the chambers.

2. The artificial sphincter of claim 1, wherein the chamber means is defined by and is comprised of at least two walls, with one of the walls facing outwardly of one of the surfaces of the band; the one wall being flexible.

3. The artificial sphincter of claim 2, wherein the one wall is also elastic.

4. The artificial sphincter of claim 3, further comprising reinforcing means on the opposite surface of the band from the one wall for preventing expansion of the opposite surface as the one wall expands.

5. The artificial sphincter of claim 4, wherein the reinforcement means comprises a substantially rigid ring for encircling the exterior of the band, when the band is wrapped around an intestine, conduit, tube, or the like, and the flexible wall faces inwardly toward the intestine, conduit, tube, or the like.

6. The artificial sphincter of claims 1, wherein the band is a strip having longitudinal ends which may be brought toward each other for encircling the intestine, conduit, tube, or the like, on which the artificial sphincter is to be used.

7. An artificial sphincter, comprising:
   - a flexible band which is bendable into a generally cylindrical figure;
   - a first row of inflatable chambers formed in said flexible band and extending generally along a circumference of said cylindrical figure, said first row of inflatable chambers including a first plurality of inflatable chambers;
   - a second row of inflatable chambers formed in said band and extending generally along a circumference of said cylindrical figure, said first row of inflatable chambers being spaced apart from said second row of inflatable chambers in the axial direction of said cylindrical figure, said second row of inflatable chambers including a second plurality of inflatable chambers, the chambers of said first plurality of chambers being staggered with respect to the chambers of said second plurality of chambers;
   - a conduit connected to at least one of said inflatable chambers for permitting an inflating fluid to be pumped into said at least one inflatable chamber; and
   - passages connecting said chambers to each other such that a substantially even fluid pressure exists in all of said chambers.

8. The artificial sphincter of claim 7, wherein each of said chambers is defined by a respective outer and inner wall and wherein each of said inner walls has a greater flexibility than its associated outer wall.

9. The artificial sphincter of claim 8, wherein each of said inner walls is elastic.

10. The artificial sphincter of claim 9, wherein each of said outer walls is non-expandable.

11. The artificial sphincter of claims 1 or 7, further including means for indicating when the pressure in said chambers reaches a predetermined value.

* * * * *